United States Patent
Devroye

(10) Patent No.: US 11,849,966 B2
(45) Date of Patent: *Dec. 26, 2023

(54) SYSTEM, APPARATUS, AND METHOD FOR FOLLICULAR UNIT EXTRACTION

(71) Applicant: Devroye Instruments Belgium, Etterbeek (BE)

(72) Inventor: Jean Devroye, Brussels (BE)

(73) Assignee: DEVROYE INSTRUMENTS BELGIUM, Etterbeek (BE)

(*) Notice: Subject to any disclaimer, the term of this patent is extended or adjusted under 35 U.S.C. 154(b) by 170 days.

This patent is subject to a terminal disclaimer.

(21) Appl. No.: 17/443,351

(22) Filed: Jul. 26, 2021

(65) Prior Publication Data

US 2021/0346047 A1    Nov. 11, 2021

Related U.S. Application Data

(63) Continuation of application No. 16/315,554, filed as application No. PCT/US2016/054149 on Sep. 28, 2016, now Pat. No. 11,071,563.

(30) Foreign Application Priority Data

Jul. 5, 2016  (BE) .................................. 2016/0123

(51) Int. Cl.
    *A61B 17/3205* (2006.01)
    *A61B 17/32* (2006.01)
    *A61B 17/00* (2006.01)

(52) U.S. Cl.
    CPC .. *A61B 17/32053* (2013.01); *A61B 17/32002* (2013.01); *A61B 2017/00398* (2013.01);
    (Continued)

(58) Field of Classification Search
    CPC ........ A61B 17/32002; A61B 17/32053; A61B 2017/00398; A61B 2017/00752; A61B 2017/320044
    See application file for complete search history.

(56) References Cited

U.S. PATENT DOCUMENTS 5,792,163 A * 8/1998 Hitzig .............. A61B 17/32053
                                                606/167
5,895,403 A    4/1999 Collinsworth
                (Continued)

OTHER PUBLICATIONS

Waw Fue Foot Pedal and Hybrid Trumpet Punch in practice (Devroye's Instruments) Sep. 15, 2016, [retrieved on Nov. 18, 2016] from the Internet: <URL:https://www.youtube.com/watch?v=F_V6TL_QlpE>.

(Continued)

*Primary Examiner* — Tuan V Nguyen
(74) *Attorney, Agent, or Firm* — Carter, DeLuca & Farrell LLP; David C. Lee

(57) ABSTRACT

Disclosed herein is a system, method, and apparatus for harvesting follicular units from an epidermis. The disclosed apparatus includes a hollow tubular structure having a central axis and a trumpet bell structure that is attached to an end of the hollow tubular structure. The trumpet bell structure terminates at a flat annular face that is substantially in a plane perpendicular to the central axis. The flat annular face has a sharp outer edge, and an inner surface of the trumpet bell structure inward from the flat annular face is smoothly varying.

18 Claims, 14 Drawing Sheets

(52) U.S. Cl.
CPC ............... *A61B 2017/00752* (2013.01); *A61B 2017/320044* (2013.01)

(56) References Cited

U.S. PATENT DOCUMENTS

| | | |
|---|---|---|
| 5,922,000 A | 7/1999 | Chodorow |
| 8,814,882 B2 | 8/2014 | Oostman, Jr. et al. |
| 8,876,847 B2 | 11/2014 | Umar |
| 9,421,030 B2 | 8/2016 | Cole |
| 2002/0103500 A1 | 8/2002 | Gildenberg |
| 2007/0156164 A1 | 7/2007 | Cole et al. |
| 2008/0051805 A1 | 2/2008 | Pinchuk |
| 2008/0234699 A1 | 9/2008 | Oostman Jr. et al. |
| 2010/0125287 A1 | 5/2010 | Cole et al. |
| 2010/0283599 A1 | 11/2010 | Ma et al. |
| 2011/0160746 A1 | 6/2011 | Umar |
| 2012/0310267 A1 | 12/2012 | Oostman et al. |
| 2013/0158584 A1 | 6/2013 | Underwood et al. |
| 2015/0018844 A1 | 1/2015 | Harris |
| 2015/0272611 A1 | 10/2015 | Harris |

OTHER PUBLICATIONS

Notification of Transmittal of the International Search Report and the Written Opinion of the International Searching Authority, or the Declaration issued in corresponding PCT Application No. PCT/US16/54149 dated Feb. 21, 2017.

Notification Concerning Transmittal of International Preliminary Report on Patentability issued by the International Bureau of WIPO dated Jan. 17, 2019 in corresponding International Application No. PCT/US2016/054149.

First Office Action issued in corresponding Appl. No. TW 201680087393.1 dated Jan. 22, 2021 (9 pages), together with English Language translation (9 pages).

\* cited by examiner

Cole J.    Artas

SYSTEM, APPARATUS, AND METHOD FOR FOLLICULAR UNIT EXTRACTION

CROSS-REFERENCE TO RELATED APPLICATIONS

The present application is a continuation of U.S. patent application Ser. No. 16/315,554, filed Jan. 4, 2019, which is a national stage of International Application No. PCT/US2016/054149, filed Sep. 28, 2016, which claims priority to Belgian Patent Application No. 2016/0123, filed Jul. 5, 2016. The entire contents of each of the foregoing applications are hereby incorporated by reference herein.

FIELD OF THE INVENTION

The disclosed technology relates to systems, apparatus, and methods for harvesting all or part of hair follicles, commonly referred to as follicular units.

BACKGROUND

During the past fifteen years, an original technique for harvesting hair grafts for performing hair grafts was developed by Dr. R. Woods, Dr. R. Bernstein and Dr. W. Rassman as well as many pioneers which include Dr. J. Cole, Dr. Jones, Dr. P. Rose, Dr. J. Harris, etc. This technique consists of using a sharp micro-tube, driven down around a small grouping of hairs called follicles. The maneuver is what is commonly called a scoring and is known as "FUE" which stands for Follicular Unit Extraction.

The skin is composed of two distinct parts—firstly the epidermis, which is superficial and elastic but strong and very difficult to penetrate without the help of a sharp instrument, and secondly a dermal part, which is deeper and looser and more easily dissected using a blunt instrument.

The technique using sharp extraction instruments (referred to as "sharp punches") is typically a two-step technique. Step 1 consists of pushing the punch around the hairs composing the follicle. Step 2: When the follicle is partially detached from the surrounding tissue, it is possible to extract it by grasping it by its tip. This maneuver corresponds to the actual follicular extraction.

The first method chosen by the majority of practitioners is to use sharp, even ultra sharp punches. The reasoning is as follows: the sharper the punch, the less it will deform the follicle within the skin during step 1 of the follicular extraction.

The majority of the punches commercially available at present are thus sharp or very sharp. There are many examples of these punches including the following references:
Restoration Robotics
U.S. Pat. No. 8,211,116 B2
Dr. John Cole
US 20070156164 A1
U.S. Pat. No. 9,204,892 B2
WO 2007/087463 A2
Dr. Sanusi Umar
US 20110160746 A1
Dr. James Harris
US 20100114118 A1
WO 2015/006658 A2

They all have the particularity of ending with a tapered triangular end, which is very aggressive. The sharp part is always directed in the same axis as the central axis of the tube, which is also the axis along which the punch moves, as shown in, for example, FIG. 2 illustrating punches according to Cole and Artas.

The practitioner, however, faces a major insoluble problem with sharp punches. Indeed, the follicles almost always have the following characteristic: they are arranged in the shape of a cone. The upper end of the cone corresponds to the output of the hair at skin level while its lower base corresponds to the follicular zone of these hairs, as shown in FIG. 1.

On the other hand, the follicle is firmly attached to surrounding structures. To be able to detach a follicle in order to extract it without damage (Step 2), the punch must be pushed in deep enough; that is to say about 3-4 mm below the epidermis. Given the conical shape of the follicle, the result of using sharp punches is often transection—that is to say, the full section of one or more of the hairs remaining captive in the donor zone. This has the effect of reducing the number of transferred hairs and thereby reducing the quality of the surgical intervention.

The orientation of the sharp punch is also crucial. Indeed, the slightest deviation from the axis of movement causes contact between the cutting portion and the hair, which causes at best a superficial abrasion, called paring, and at worst a full section of hair remaining in the donor zone, called a transection.

Consequently, it is often necessary to reduce the depth of the incision made with a sharp punch, such as limiting the incision depth to 2 mm below the epidermis, and/or to increase the diameter of the punch to obtain grafts with a low transection rate. This has the effect of increasing the size of scars and of damaging the follicles adjacent to the one being extracted. Furthermore, when a sharp punch only slightly penetrates the dermis, the extraction process (Step 2) is slowed with a risk of damaging the follicles during extraction. So this lengthens the overall duration of the intervention.

Numerous specific systems to limit the depth of insertion of sharp punches have been proposed. For example, Dr. John Cole has developed such systems on all of his follicular extraction instruments.

Even so, it is common to find that despite the efforts of practitioners, the rate of removed follicles that are damaged or completely cut is often significant and sometimes enormous. It is not uncommon to find harvests with more than 20 to 40% of damaged hairs or follicles.

The second method developed about 15 years ago has been to subdivide Step 1 into two steps with the use of two different punches. This second method was named the "3 step" technique. The first step is the very superficial cutting of the epidermis with the aid of a sharp punch. The second step is to then use a blunt or dull punch to dissect the dermal tissue around the hairs without damaging them. And the third step is the actual extraction. The technique dates from 2004 and was invented by Dr. James Harris. FIG. 3 illustrates an example of Dr. Harris' instrument.

This same principle was adopted by the Restoration Robotics Company, which still currently uses a system consisting of two punches on its Artas robot—one sharp punch is enclosed in a blunt punch that slides around it, as shown in FIG. 4. The two punches work successively.

There are disadvantages to the two-step technique and the 3-step technique. Accordingly, there is continued interest in development of improved follicular extraction instruments.

SUMMARY

The present invention relates to a device and a method for harvesting all or part of follicles commonly called follicular units. The disclosed device includes a hollow tube-like punching tool suitable for producing cores in the scalp. In one embodiment, the tool has a flat end substantially perpendicular to the tube central axis, with the flat end terminating in a sharp external cutting edge. The interior of the tube is rounded similar to the shape of a trumpet, and therefore the tool is referred to herein as a "trumpet punch" or "hybrid trumpet punch."

This disclosed tubular tool is commonly called a punch and is classified under a very limited group of hybrid punches that are not very sharp. In one aspect of the disclosed technology, the punch is driven by a dedicated system that includes a foot pedal and a motor. This pedal activates the motor, which is coupled to the punch. This pedal produces movement of the motor and, therefore, movement of the punch. The pedal is not a simple on-off switch. Rather it triggers an oscillatory rotation whose speed is proportional to the pedal stroke.

In one aspect of the disclosed technology, An apparatus for harvesting hair grafts from an epidermis includes a hollow tubular structure having a central axis and a trumpet bell structure attached to an end of the hollow tubular structure. The trumpet bell structure terminates at a flat annular face that is substantially in a plane perpendicular to the central axis. The flat annular face has a sharp outer edge, and an inner surface of the trumpet bell structure inward from the flat annular face is smoothly varying.

In one embodiment, the flat annular face is at an angle relative to the central axis of 85° to 95° or 87° to 93° and is not perpendicular to the central axis. In one embodiment, the flat annular face is perpendicular to the central axis. In one embodiment, the flat annular face has a thickness of 50 µm or more. In one embodiment, the flat annular face has a thickness of 80 µm or 100 µm or more. In one embodiment, the hollow tubular structure has an outer diameter between 0.7 mm and 1.4 mm and a wall thickness between 50 µm and 150 µm. The sharp outer edge of the flat annular face of the trumpet bell structure has an outer diameter that is greater than the outer diameter of the hollow tubular structure by at most 200 µm. In one embodiment, the hollow tubular structure includes one or more windows.

In one embodiment, the trumpet bell structure has a height of less than 1000 µm. In one embodiment, the trumpet bell structure has a height of less than 500 µm. In one embodiment, the trumpet bell structure has a height between 300 µm and 500 µm.

In one embodiment, the inner surface of the trumpet bell structure inward from the flat annular face is substantially shaped as a half catenoid. In one embodiment, the sharp outer edge of the trumpet bell structure has a toothed configuration having one or more teeth. In one embodiment, the sharp outer edge of the trumpet bell structure is substantially circular.

In one aspect of the disclosed technology, the disclosed apparatus includes a motor coupled to the trumpet bell structure that causes the trumpet bell structure to rotate successively between clockwise and counterclockwise rotations. In one embodiment, the motor is capable of being controlled to vary an amount of rotation of the trumpet bell structure such that each clockwise or counterclockwise rotation is capable of rotating more than 30° but less than 360°.

In one aspect of the disclosed technology, the disclosed apparatus includes a pedal coupled to the motor. In one embodiment, the pedal controls rotation of the trumpet bell structure such that a depression of the pedal corresponds to a proportional change in a speed of the rotation of the trumpet bell structure. In one embodiment, a depression of the pedal corresponds to an exponential increase in a speed of the rotation of the trumpet bell structure. In one aspect of the disclosed technology, the pedal is configurable to adjust the exponential correlation between the depression of the pedal and the increase in the speed of the rotation of the trumpet bell structure, and the pedal is configurable to select among two or more exponential correlations. In one aspect of the disclosed technology, the speed of the rotation of the trumpet bell structure is adjustable between 60 clockwise-counter-clockwise rotations per minute and 300 clockwise-counter-clockwise rotations per minute.

In one embodiment, the apparatus includes a battery powering the motor, and the pedal is coupled to the motor wirelessly. In one embodiment, the apparatus includes a battery powering the pedal. In one embodiment, the pedal includes a visual indicator that provides a warning before the battery is completely depleted.

In one embodiment, the apparatus includes a robot for assisting surgical hair transplantation, and the hollow tubular structure and the trumpet bell structure are coupled to the robot. In one embodiment, the apparatus includes a dental handpiece, and the hollow tubular structure and the trumpet bell structure are coupled to the dental handpiece.

In one aspect of the disclosed technology, the apparatus includes a suction chamber attached to the end of the hollow tubular structure opposite the trumpet bell structure and a suction device is coupled to the suction chamber.

In one aspect of the disclosed technology, the apparatus includes a size indicator which indicates a size of the trumpet bell structure. In one aspect of the disclosed technology, the apparatus includes a plurality of depth indicators on the hollow tubular structure which indicate depth at which the trumpet bell structure has been inserted below an epidermis.

In one aspect of the disclosed technology, an apparatus for harvesting hair grafts from an epidermis includes a hollow tubular structure that terminates at a rounded base. The base is substantially perpendicular to a central axis of the hollow tubular structure. An annular lip surrounds the end portion of the hollow tubular structure. The annular lip has an annular ledge that is substantially perpendicular to an outer surface of the hollow tubular structure. The annular lip also has a transition portion that smoothly connects the annular ledge to the rounded base of the hollow tubular structure. In one embodiment, the transition portion is at an angle relative to the central axis of 30° to 60°.

In one embodiment, the tool can be housed in a handpiece or device used in the dental industry and can be capable of being sterilized. The disclosed technology can decrease the transection of follicles, i.e., the partial or complete cut of one or more hairs composing this follicle, and thus greatly improve the quality of the FUE hair transplant surgery and the number of harvested grafts. The number of missing grafts, that is to say, the number of grafts completely transected or buried in the skin, therefore, decreases dramatically.

DETAILED DESCRIPTION

The disclosed technology relates to hair follicle harvesting system, method, and apparatus that greatly reduces the rate of transection and missing grafts, even when using smaller diameter punches, and that increases harvesting rate with little or no damage to follicles during the extraction step. The system includes various parts. In particular, a pedal activates a motor, which communicates therewith via a cable or wirelessly. A handpiece can be fitted to the motor, and the pedal triggers movement of a punch held in the handpiece via a chuck.

A tool according to the disclosed technology combines in a single punch two seemingly opposing characteristics: a punch sharp enough to penetrate the epidermis easily and at the same time ensuring that this punch is sufficiently gentle so as to reduce damage to the hairs when it plunges into the dermal portion of the skin.

In accordance with one aspect of the disclosed technology, the disclosed tool positions an annular cutting edge at the outer perimeter of the end of the tool and places it in a plane perpendicular to the central axis of the punch. A tool according to one embodiment of the disclosed technology has a hollow tubular structure with a central axis and an end structure in the shape of a trumpet bell. The trumpet bell structure terminates in a substantially flat and ring-like/annular face extending substantially in a plane perpendicular to the central axis. The substantially flat annular face has a sharp outer edge, which can be continuous and substantially circular, or can be non-circular and jagged or tooth-like.

Figure 1:
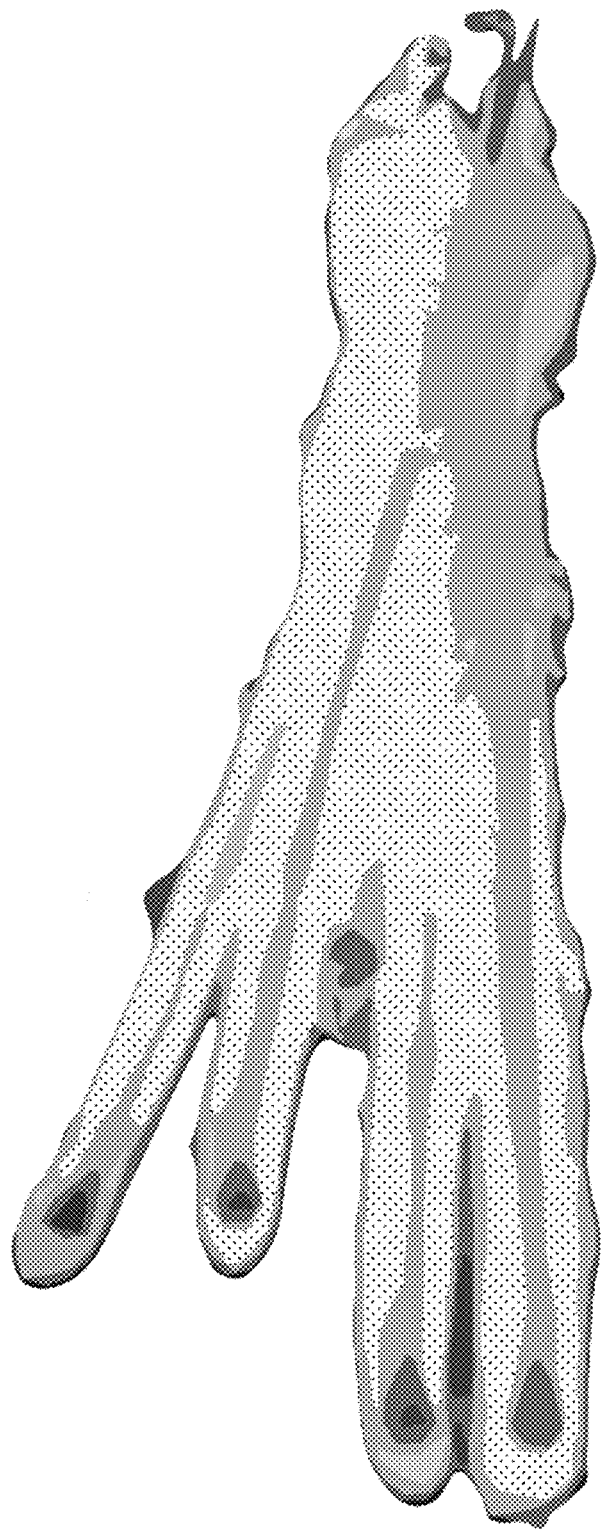
FIG. 1 schematically shows a follicle model with its classic conical shape.
Figure 2:
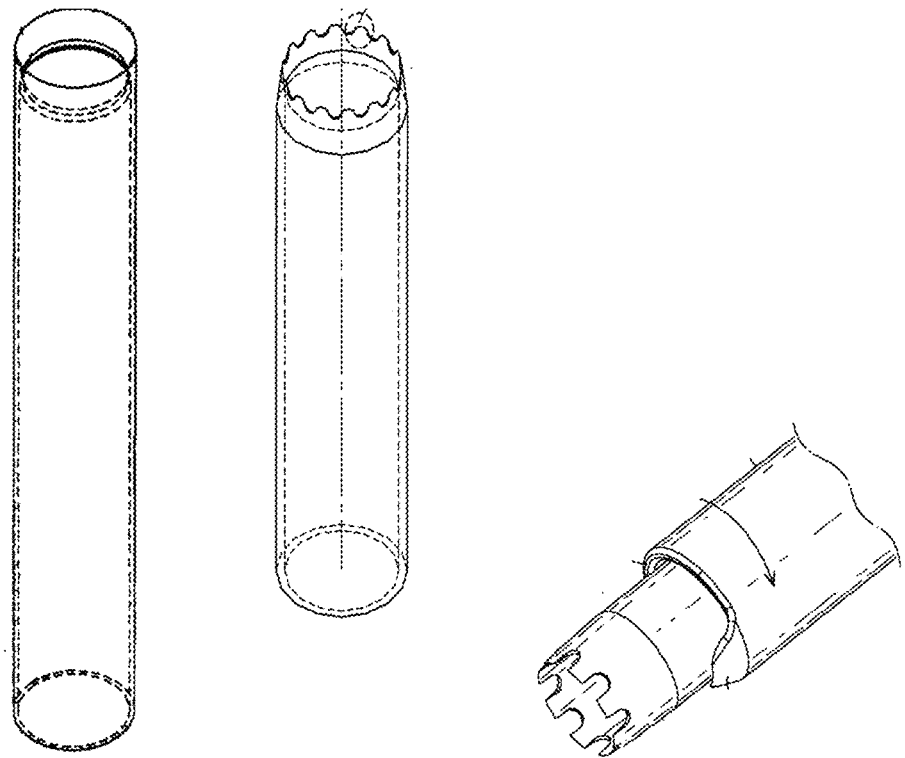
FIG. 2 shows examples of sharp punches according to Dr. John Cole and Artas.
Figure 3:
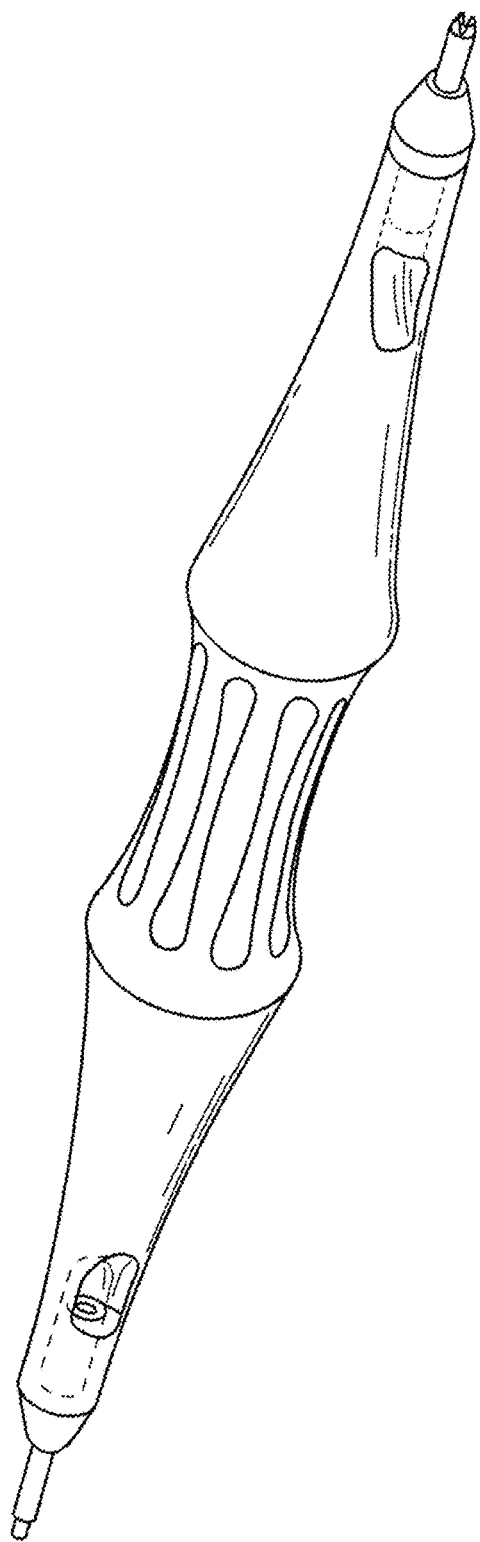
FIG. 3 shows an example of an extracting device according to Dr. James Harris comprising a handle, a sharp punch on one side of the handle, and an extraction punch on the other side of the handle.
Figure 4:
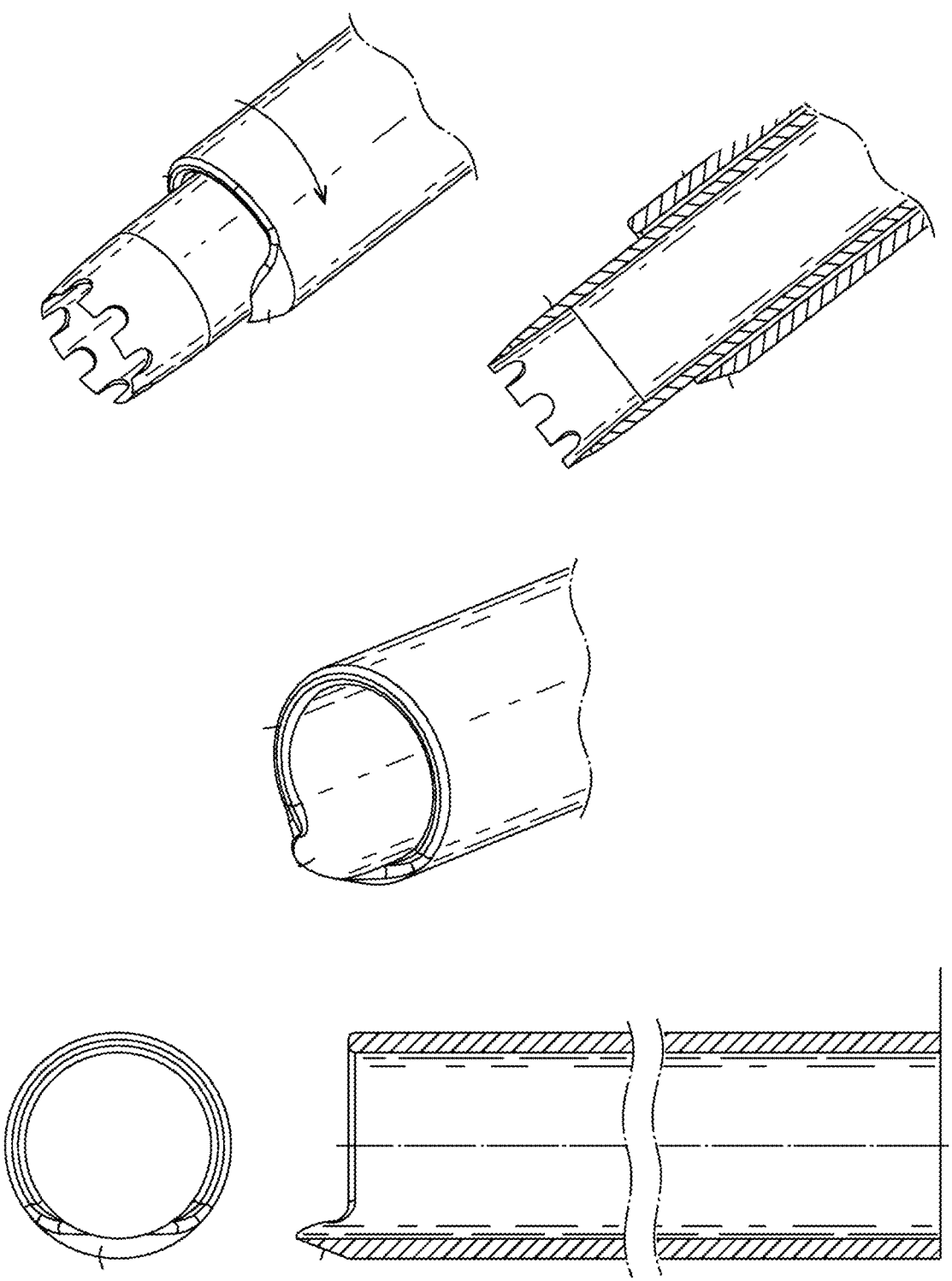
FIG. 4 shows an example of a tool from Restoration Robotics with two punches slidably mounted.
Figure 5:
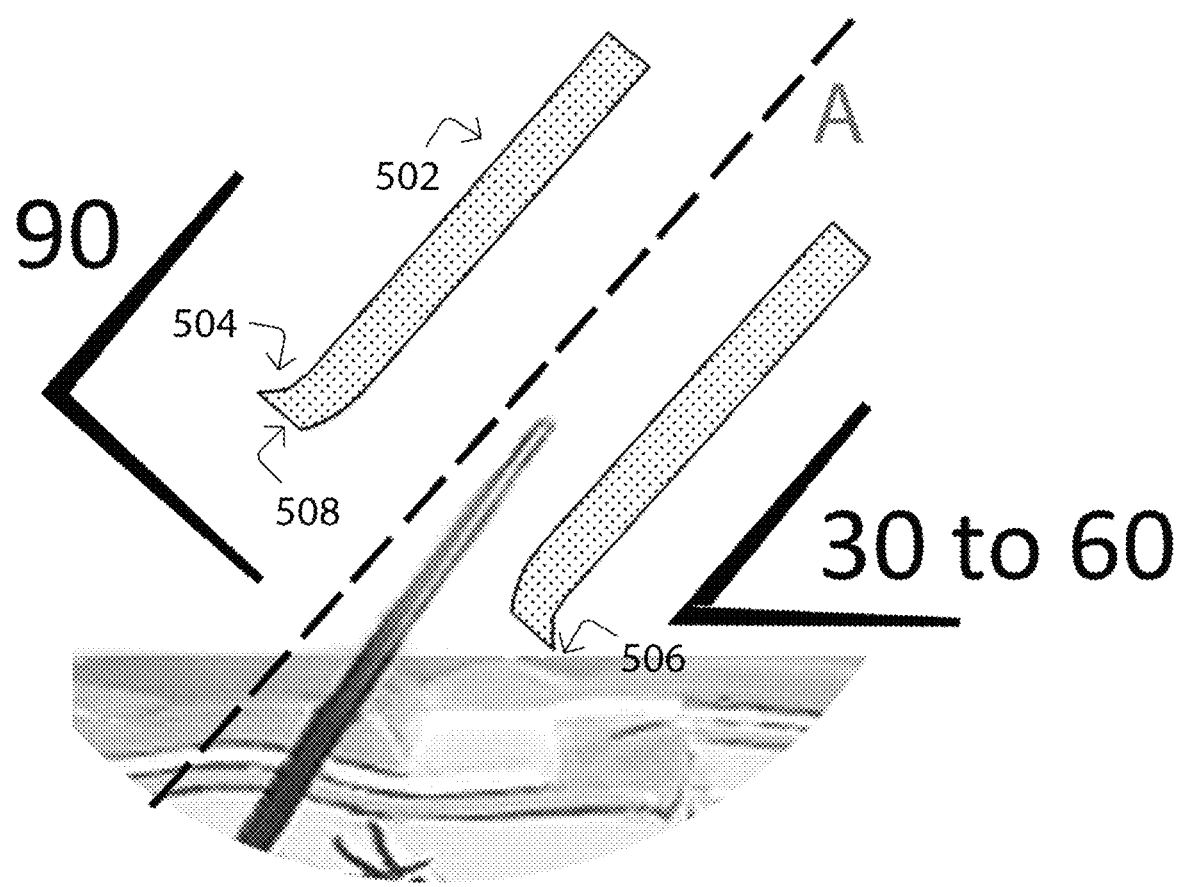
FIG. 5 shows an example of use of a tool according to the disclosed technology, during the epidermis-cutting step.

The operation of the tool according to the disclosed technology is shown in FIG. 5, which illustrates a cross-section of a hollow tubular structure 502 and a trumpet bell structure 504 of one embodiment of the disclosed punch. The trumpet bell structure 504 is shaped such that it appears as a funnel to the hair. The cutting edge 506 is located on the outer edge of the flat annular face 508 of the trumpet bell structure and is located in a plane that is perpendicular to the central axis A of the hollow tubular structure 502.

If this trumpet-shaped end structure is placed perpendicularly to the epidermis, the flat face 508 of the tool is supported on the skin in such a way that the rotation of the tool relative to its central axis in no way cuts the epidermis. On the other hand, if one pivots the tool so that its end portion is positioned in a plane at an angle of 30 to 60° with respect to the plane of the epidermis, the sharp outer edge 506 is in contact with the epidermis and is capable of marking and cutting the skin during a rotary movement of the tool about its central axis.

A punch according to the disclosed technology is positioned such that the skin is not approached perpendicularly but obliquely. The sharp outer edge 506 of the end of the punch can therefore easily cut into the epidermis, which, as previously described, can be resistant. Once this barrier is passed, the movement of the punch can be controlled in order to move it parallel to the axis of the hairs, and therefore the cutting portion (outer edge) also moves in such a way that it is remote from the hair to be harvested and therefore cannot damage the hairs/grafts that are harvested. In addition, these hairs are directed towards the center of the punch, as in a funnel, and touch the round inner portion of the punch, as shown in FIG. 5, which greatly reduces, or even eliminates, their transection and also reduces the damage that sharp punches usually cause.

Because the disclosed punch has both sharp and unsharp characteristics, they are referred to herein as "hybrid trumpet punches." Because the inside of the punch is smooth, it is possible to reduce the size of the punch used, and thus to reduce the injuries/scars around the hairs.

In one aspect of the disclosed technology, movement of the punch is a slow movement between approximately 60 and 300 revolutions per minute. In one embodiment, the movement is an oscillating movement such that rotation successively changes direction after having travelled a 30 and 360 degree course. The pedal which is included in the disclosed system (discussed below herein) allows one to change the speed of this movement with more or less pressure on the foot pedal.

The disclosed punch operates to harvest intact human follicular units during a hair transplant surgery. The disclosed harvesting tool has some of the beneficial characteristics of conventional sharp punches without being a sharp punch.

Figure 6:
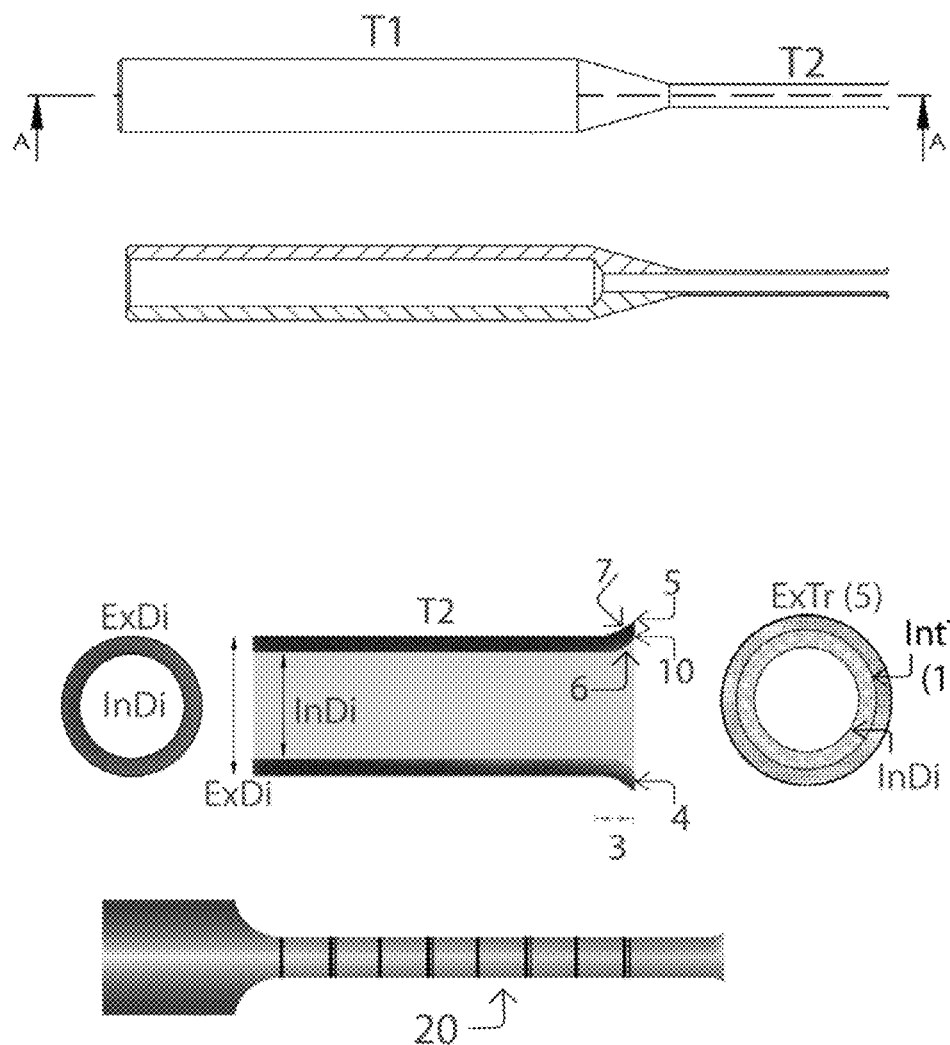
FIG. 6 shows exemplary views of a tool according to one embodiment of the disclosed technology.

Referring to FIG. 6, the hybrid trumpet punch according to the disclosed technology can be a single piece that is made from the stainless steel. It can include two hollow tubular structures. The wider proximal tubular structure (T1) can have an outer diameter of approximately 2.34 mm, which makes it compatible to fit in most dental handpieces. In one embodiment, the wider proximal tubular structure can serve as a suction chamber and can be housed in a dental handpiece that provides suction. In one embodiment, the hybrid trumpet punch can be housed in a dental handpiece that does not provide suction, and suction can be provided separately from the handpiece.

The disclosed tool includes a narrower, distal hollow tubular structure (T2) with a central axis and an end structure 3 in the shape of a trumpet bell. The trumpet bell terminates with a substantially flat and annular/ring-like face 4 that extends substantially in a plane perpendicular to the central axis of the punch and having a sharp outer edge 5. In one embodiment, the sharp outer edge 5 can be substantially circular and continuous. In one embodiment, the sharp outer edge 5 can be non-circular and can include one or more teeth.

Figure 9:
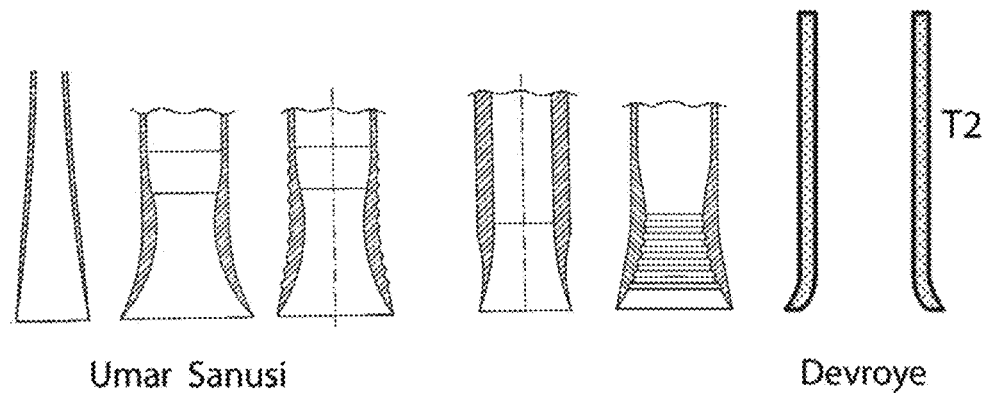
FIG. 9 shows a comparison of a punch according to the disclosed technology and a punch according to Dr. Sanusi Umar.
Figure 10:
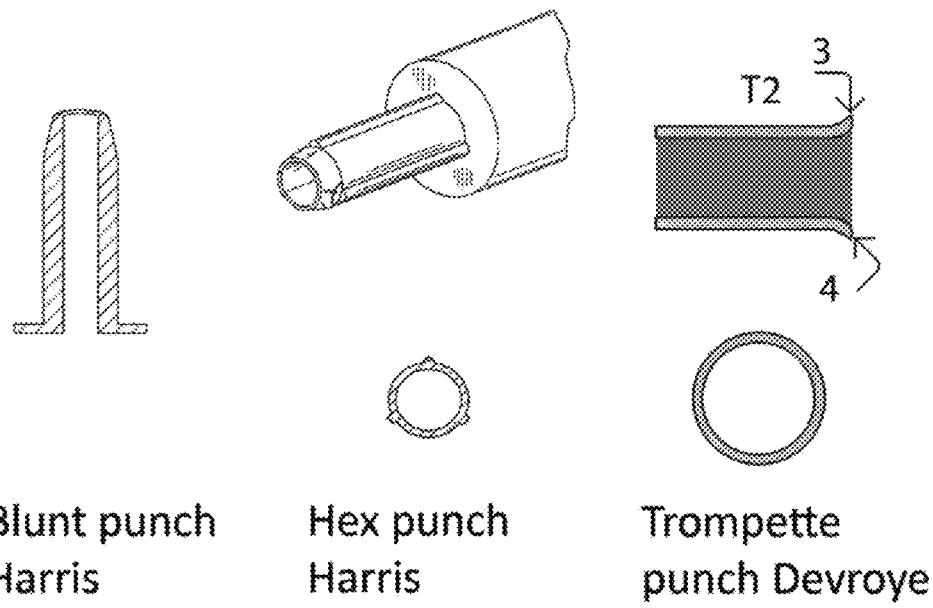
FIG. 10 shows a comparison of a punch according to the disclosed technology and punches according to Dr. James Harris.
Figure 11:
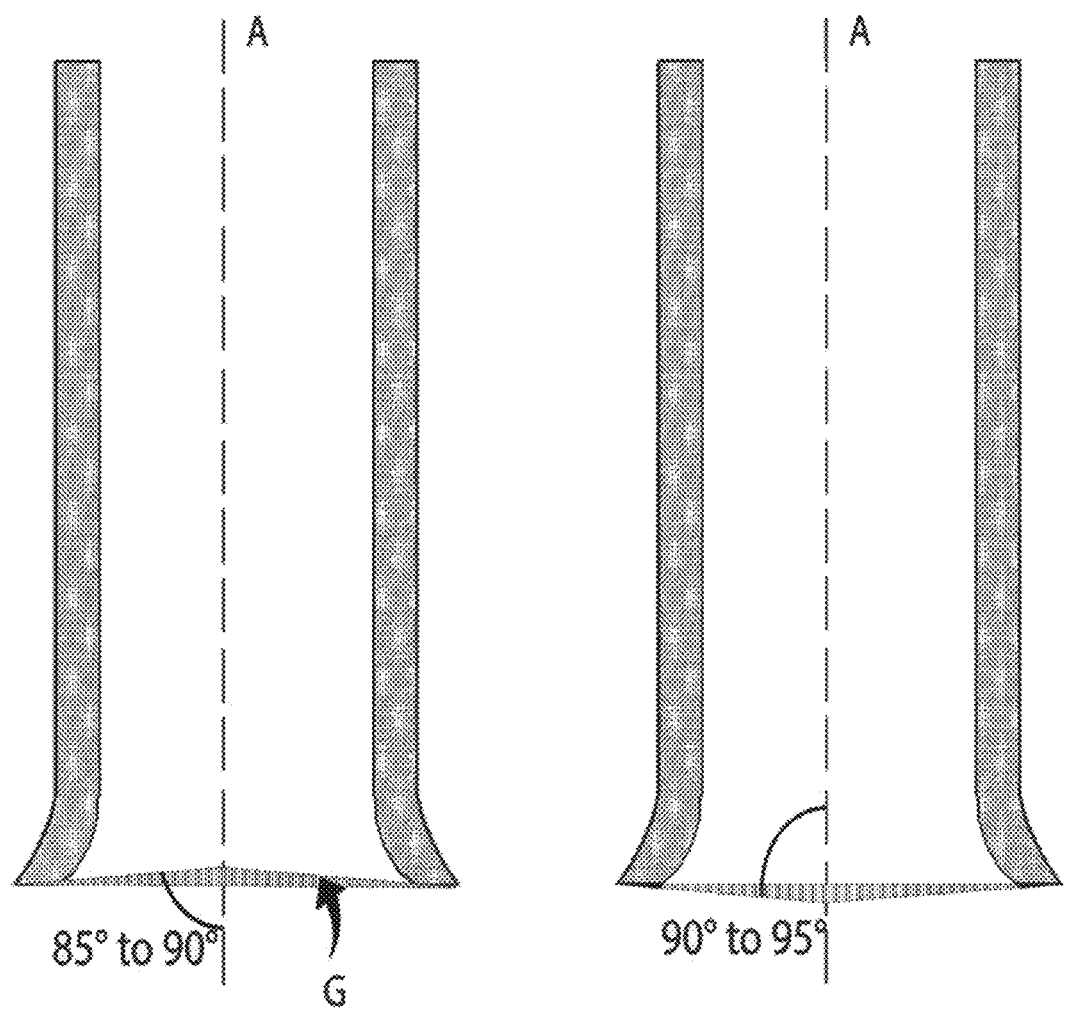
FIG. 11 shows examples of cross-sections of trumpet punches according to embodiments of the disclosed technology.

Referring to FIGS. 6-12, a tool according to the disclosed technology has one or more of the following features. The tool includes a central axis, while the substantially flat and annular face 4 at the base portion of the tool, which is configured to be at an angle relative to the central axis that is between 85 to 95°, as shown in FIG. 11. In one embodiment, the angle can be between 87° to 93°. In one embodiment, the flat annular face 4 can be perpendicular to the central axis, as shown in FIG. 6.

In one embodiment, the substantially flat, annular or ring-like face 4 has a wall thickness between 50 μm and 100 μm, which is the difference between ExTr and IntTr. In one embodiment, the hollow tubular structure T2 has an external diameter ExDi between 0.7 mm and 1.4 mm and has a wall thickness between 50 and 150 μm. In one embodiment, the external diameter ExTr at the end of the trumpet bell structure is greater than the outer diameter ExDi of the hollow tubular structure T2 by approximately 50 to 150 μm. In one embodiment, the external diameter ExTr at the end of the trumpet bell structure is greater than the outer diameter ExDi of the hollow tubular structure T2 by no more than 200 μm.

In one embodiment, the inner edge 10 (InTr) of the flat annular face 4 of the trumpet bell structure is substantially aligned with the outer surface of the hollow tubular structure T2 with diameter ExDi. Accordingly, the inner edge 10 of the flat annular face 4 of the trumpet bell structure IntTr therefore has a diameter equal to or close to the diameter ExDi.

In one embodiment, the trumpet bell shaped structure 3 has a length of less than 1000 μm. In one embodiment, the trumpet bell shaped structure 3 has a length between 500 and 300 μm.

With continuing reference to FIG. 6, the trumpet bell structure 3 has a smoothly curved inner surface 6 that smoothly connects to the inner surface of the hollow tubular structure T2. In one embodiment, the inner surface 6 of the trumpet bell structure 3 is substantially in the shape of a half catenoid.

In one embodiment, the outer edge 5 of the flat annular face 4 of the trumpet bell structure is sharp. The flat annular face 4 can be beveled to enhance the sharpness of the outer edge. The inner edge 10 of the flat annular face 4 of the trumpet bell structure can have a less abrupt angle or can be rounded.

Figure 7:
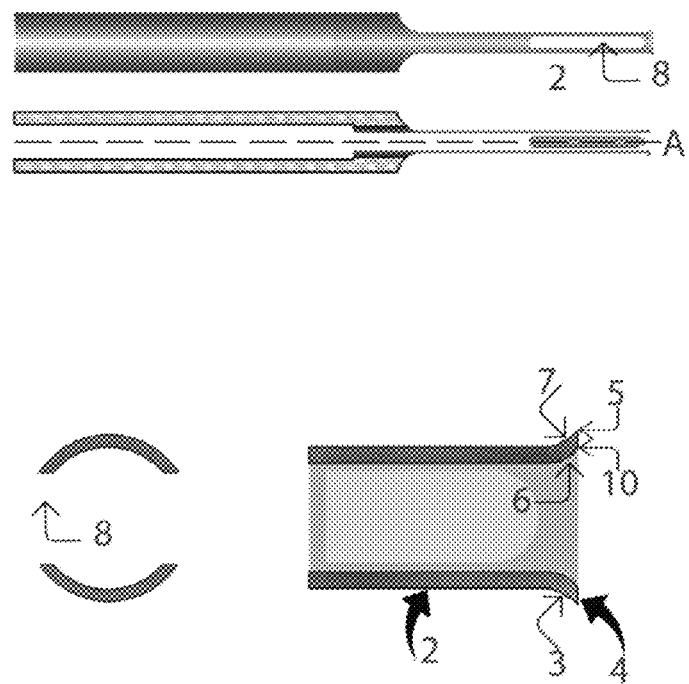
FIG. 7 shows exemplary views of a tool according to another embodiment of the disclosed technology, in which windows are provided in the tool.
Figure 7:
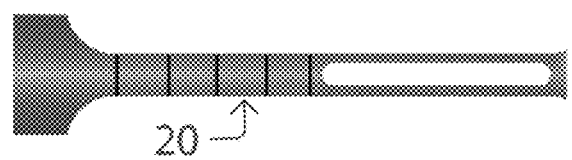

Referring now to FIG. 7, the hollow tubular structure may have one or more windows 8 that provide a view of the hair to be harvested within the hollow tubular structure. In the illustrated embodiment of FIG. 7, two windows 8 opposite each other and positioned 180 degrees apart are arranged on the lower part 2 of the hollow tubular structure just above the trumpet bell structure.

The windows of FIG. 7 provide two advantages. As mentioned above, the windows allow a view of the hair and thus allow a user to accurately position the punch around the hairs. Secondly, friction between the hairs and the punch is reduced due to decreased inner surface area because of the windows, thereby allowing the punch to be driven deeper into the dermis while avoiding a phenomenon known as the "missing graft" (graft failure). A missing graft can occur when a conventional punch is inserted too deeply and causes twisting of the follicle, which can lead to a shortening of the latter and to "suction" inside the skin. The graft can disappear completely from the operating field, and it is virtually impossible to recover it.

Figure 8:
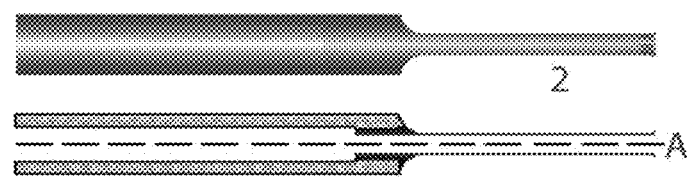
FIG. 8 shows exemplary views of a tool according to the disclosed technology in which teeth are provided on the outside rim of the trumpet punch.
Figure 8:
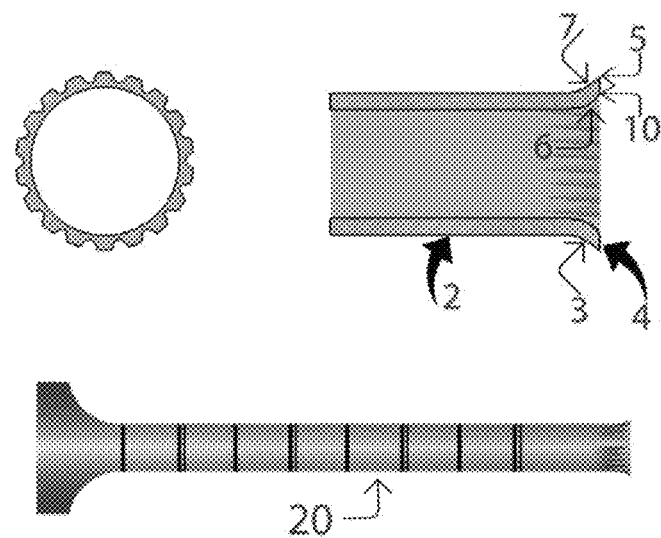

FIG. 8 shows another embodiment of the disclosed tool. In the illustrated embodiment, the tool can include teeth arranged on the outer surface of the hollow tubular structure 2 and/or on the outer surface of the trumpet bell structure 3. In one embodiment, the outer surface can include between 20 to 30 teeth. The illustrated toothed punch can be used when the skin resistance is particularly significant. The embodiments of FIGS. 7 and 8 can be separate, as illustrated, or can be combined such that a tool can have both windows and teeth.

Figure 12:
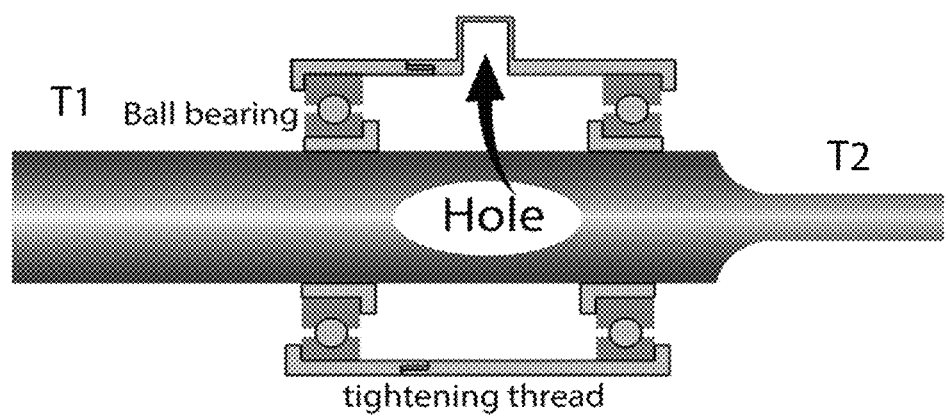
FIG. 12 shows an example of a suction system external to the punch, in accordance with aspects of the disclosed technology.

Referring now to FIG. 12, the disclosed technology can include a suction chamber T1 attached to the hollow tubular structure T2. This suction chamber can be connected to a pump (not shown). When the punch is housed in a handpiece, the pump can be located away from the handpiece or attached to the handpiece. This suction can aspirate the blood that pools in the holes made in the skin. This also allows lightly suctioning the follicle during extraction and securing it by preventing it from rotating inside the punch.

Referring to FIGS. 6-8, in one aspect of the disclosed technology, size indicators such as line or circular markings can be affixed to the outer surface of the wider tubular structure T1 to indicate the size of the punch to the operator. Such size can correspond to the outer diameter of the flat annular face of the trumpet bell structure (ExTr). It, therefore, corresponds to the actual size of the hole created by the distal part of the narrower tubular structure (T2). In accordance with the disclosed technology, the hybrid trumpet punches can have the following sizes: size 1: 0.7 mm; size 2: 0.75 mm; size 3: 0.8 mm; size 4: 0.85 mm; size 5: 0.9 mm; size 6: 0.95 mm; size 7: 1 mm; size 8: 1.05 mm; size 9: 1.1 mm; size 11: 1.2 mm. Other sizes not expressly stated herein are contemplated and are encompassed by the disclosed technology.

In one aspect of the disclosed technology, the thickness of the tubular structure wall is adapted to its diameter. In one embodiment, the wall thickness can range from 0.08 mm (80 μm) and 0.12 mm (120 μm).

For example, a punch of 0.9 mm will have an external diameter of 0.9 mm for face of the trumpet bell structure. Correspondingly, the hollow tubular structure T2 will have an inner diameter of 0.75 mm and an outer diameter of 0.9 mm.

In one aspect of the disclosed technology, and referring to FIGS. 6-8, the tubular structure T2 can include depth indicators 20, such as graduated markings, that indicate the depth at which the punch is located below the surface of the skin. In one embodiment, a marking can be placed every 500 μm along the outer surface of the tubular structure T2.

Referring to FIG. 7, the windows 8 can be positioned just above the trumpet bell structure and the size of the windows can depend on the size of the tubular structure T2. For example, the size of the windows 8 can increase with the diameter of the tubular structure T2. For example a punch of size 0.9 mm can have two windows of size 3 mm by 0.6 mm.

What has been described above herein is a tool for harvesting follicles having a tubular structure attached to a trumpet bell structure. In one embodiment, as illustrated in FIG. 9, the hollow tubular structure T2 can have a constant inner and outer diameter and a constant wall thickness. This disclosed tool differs from punches disclosed by Dr. Umar Sanusi, which have varying inner and/or outer diameters. Furthermore, the punches of Dr. Umar are sharp punches whose cutting edges are not substantially perpendicular to the central axis of the punch. The disclosed trumpet punch, in contrast, has a cutting edge that is substantially perpendicular to the central axis of the punch.

In one embodiment, as illustrated in FIG. 10, the disclosed trumpet bell structure 3 flares outward from the hollow tubular structure T2 to which it is attached, and the annular face 4 of the trumpet bell structure is substantially circular. This disclosed tool differs from punches disclosed by Dr. James Harris, which taper inward at the end or do not taper at all at the end.

Figure 15:
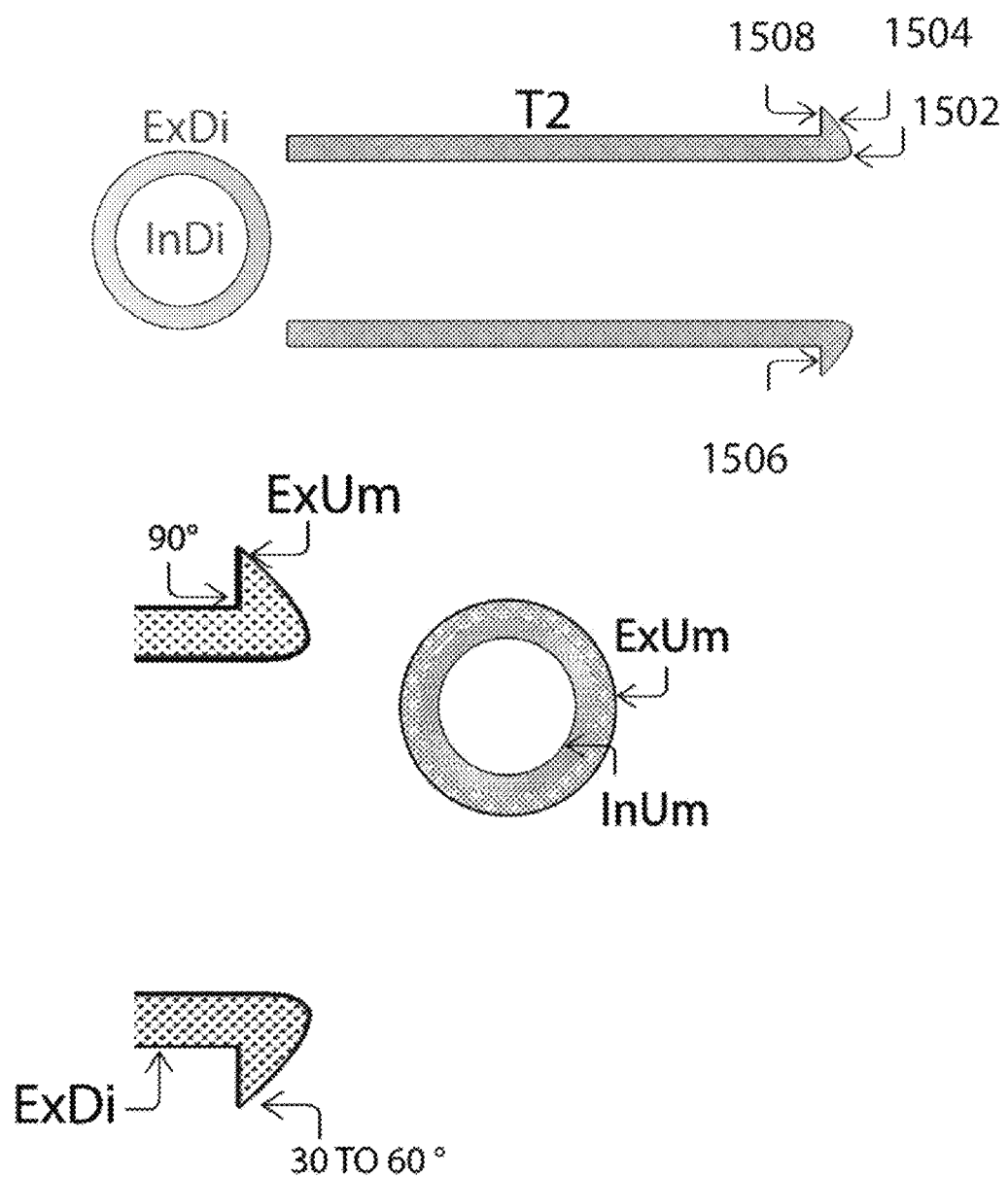
FIG. 15 shows exemplary views of a tool according to another embodiment of the disclosed technology.

What will now be described is another embodiment of a tool in accordance with the disclosed technology. Referring to FIG. 15, the illustrated tool includes a tubular structure T2 that terminates at an end 1502 with a rounded annular face. Surrounding the end portion is an annular lip 1504 that includes an annular ledge 1506. In one embodiment, the ledge 1506 is perpendicular to the central axis of the hollow tubular structure T2. The outer edge 1508 of the ledge can connect smoothly with the rounded annular face 1502 of the end of hollow tubular structure such that the end 1502 of the disclosed tool remains rounded and smooth. Various aspects of the tools illustrated in FIGS. 6-8 are applicable to the punch of FIG. 15, including, for example, various dimensions of walls and diameters, such as the wall thickness between ExDi and InDi. For example, the annular ledge can have a diameter ExUm that is greater than the diameter ExDi of the hollow tubular structure by no more than 100 to 200 µm.

Figure 13:
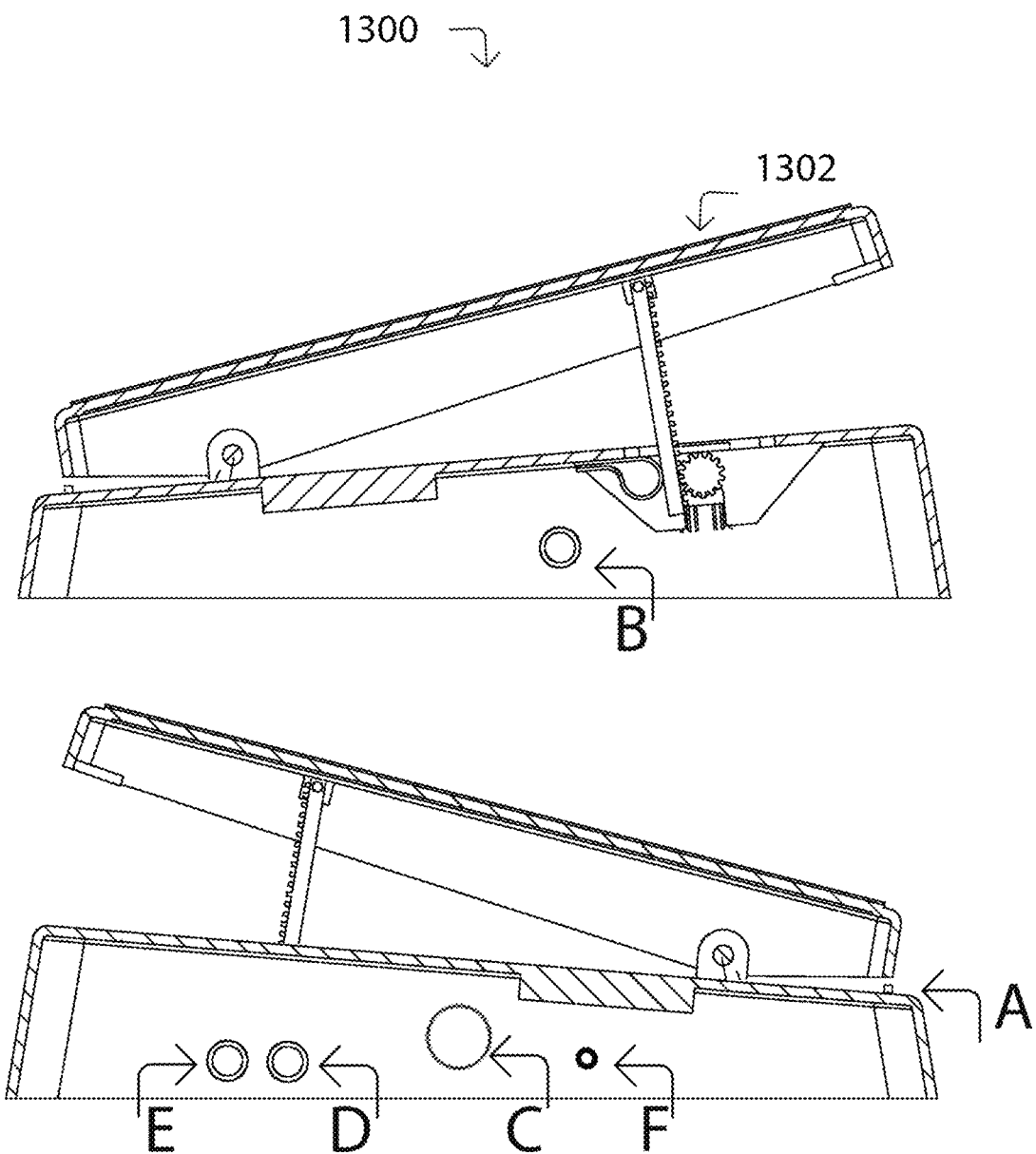
FIG. 13 shows examples of a pedal equipped with various control buttons, in accordance with aspect of the disclosed technology.
Figure 14:
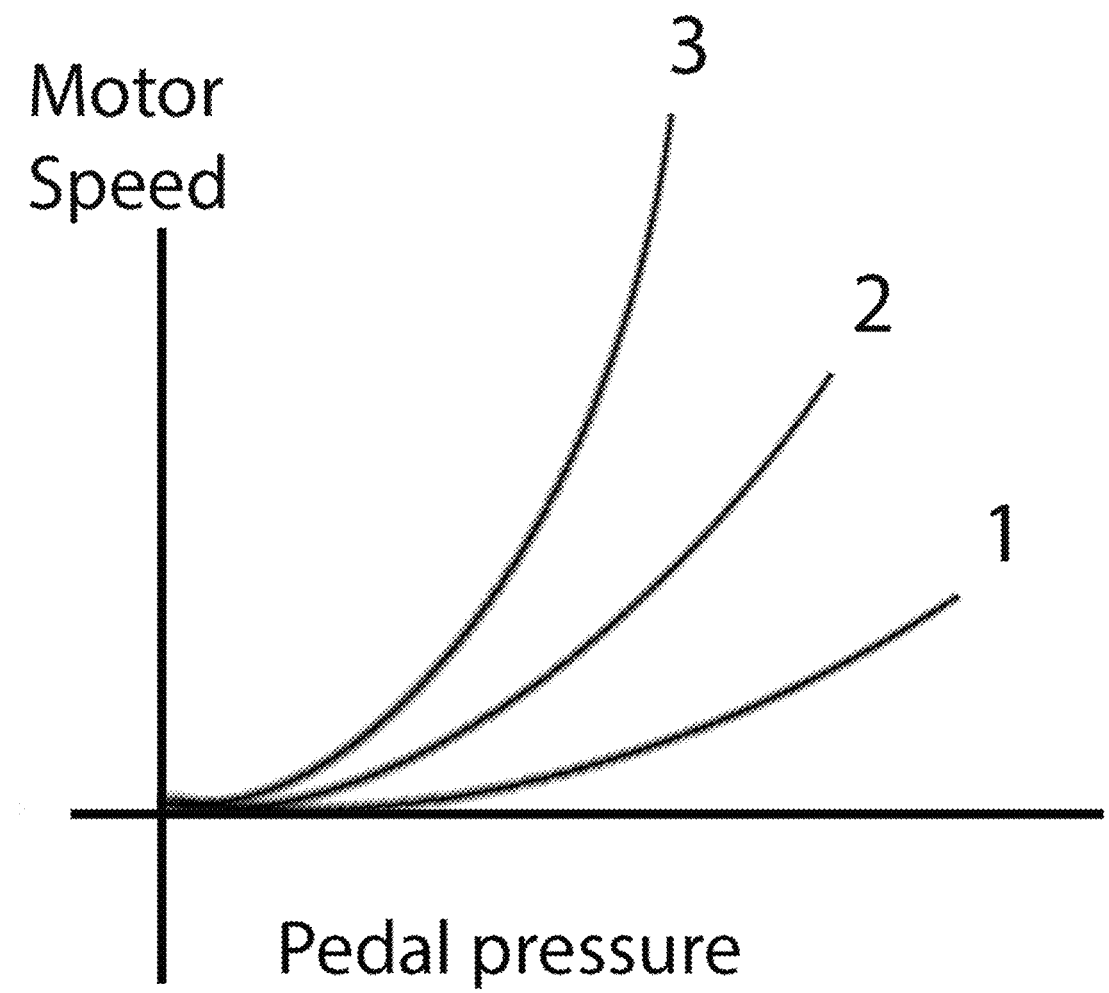
FIG. 14 shows examples of correlation between pedal pressure and motor speed, in accordance with different embodiments of the disclosed technology.

What will now be described in connection with FIGS. 13 and 14 are parts of the disclosed tool motorizing the disclosed punch. FIG. 13 is an illustration of a foot pedal 1300 in accordance with one embodiment of the disclosed technology. The pedal includes a top plate 1302 which pivots and can travel a distance of, for example, 5 cm. The pedal can control rotation of the disclosed punch through a motor (not shown), and the depression of the pedal top plate 1302 enables the rotational speed of the punch to be varied with precision. Outlet B provides a port or jack or connection through which the foot pedal can communicate with and power the motor for rotating the disclosed punch. In another embodiment, the foot pedal can communicate wirelessly with the motor, such as by Bluetooth or another wireless protocol, and the motor can have a separate power source.

In one embodiment, the pedal 1300 can include various knobs or buttons or interfaces, each having different functions, as described in the following disclosure.

In one embodiment the foot pedal 1300 can be powered by a battery (not shown). The first button A, located below the pedal, allows powering of the motor only when the pedal is actively used. In other words, button A serves to prevent powering of the motor when the pedal is not actively used. In this way, the battery is very slightly discharged when the foot pedal 1300 is not actively used. In this manner, the batteries can operate for extended periods without recharging. In one embodiment, the battery can provide power for 72 hours without recharging.

In the illustrated embodiment, there foot pedal 1300 can provide an indication that the battery will be imminently discharged, which provides a degree of protection against the complete discharge or depletion of the batteries. In one embodiment, a red flashing button (not shown) can warn of impending discharge or depletion of the battery and can notify a user to charge the batteries. In one embodiment, the batteries can be recharged with a charger (not shown) that plugs into the socket F. The plug can be compatible with all regions of the world.

In the illustrated embodiment, button C enables the very precise of the amount of angular rotation of the punch. In one embodiment, the disclosed punch can rotate around its axis alternating successively between clockwise rotation and counter-clockwise rotation. In one embodiment, each clockwise rotation or counter-clockwise rotation can be between 30° and 360°, and button C is used to adjust the number of degrees of this angular rotation in each direction. In some embodiments, the angular rotation can be more than 360°.

In one aspect of the disclosed technology, the rotation speed or angular velocity of the punch can be controlled. With reference also to FIG. 14, the illustrated graph shows that displacement of the foot pedal can increase the angular velocity of the punch rotation exponentially depending on the intensity of the thrust on the pedal. The foot pedal can include different correlations between pedal pressure and the motor driving the rotation of the punch, as illustrated. Knob D, illustrated in FIG. 13, can be used to modify the correlation or progression curve. In one embodiment, turning the knob D clockwise straightens the curve (for example, 1 towards 2 towards 3) which allows for greater responsiveness of the pedal.

In one embodiment, button E allows adjusting the level of the initial starting speed of the motor. It does not alter the progression of the motor speed as shown in FIG. 14 and is a separate functionality. Button E can be set at the first use and need not be set again unless a different motor is connected.

Accordingly, what has been described above herein is a pedal, activated by the operator's foot, which launches the rotation of the punch and controls it in a precise manner. In use, the disclosed system can limit the movements of the punch when necessary. When piercing the epidermis as shown in FIG. 5, a speed between 60 and 300 clockwise-counter-clockwise rotations per minute can be achieved with the disclosed system. Then, when the punch penetrates into the deep dermis, the rotational speed can be decreased further. The disclosed system also allows, via the adjusting knobs, to change the amount of angular rotation in order to minimize the twisting of the follicle, which results from friction between the graft and the inner part of the punch. The recommended amount of angular rotation in the clockwise direction and the counter-clockwise direction is between 30° and 360°, depending on the quality of the skin. It is common to successfully extract a graft with a succession of about a dozen clockwise and counter-clockwise oscillations.

The disclosed pedal can include circuitry, processors, microcontrollers, programmable logic devices, ASICS, memory, software, firmware, and/or other software or hardware to perform the disclosed operations. The disclosed buttons and knobs on the pedal are exemplary and other interfaces are contemplated, such as switches, slides, and touch screens.

A punch in accordance with the disclosed technology is capable of extracting between 500 and 1000 grafts before requiring light sharpening and between 4000 and 8000 grafts before being replaced.

A punch according to the disclosed technology can be driven much deeper than a sharp punch of an equivalent diameter, with lesser risk of damage. This penetration depth may be equal to the length of a hair follicle, such as between 3 and 5 mm. The result is the ability to obtain high quality grafts, with very low transection rate and, at the same time, a higher number of hairs per graft (follicular density) than with a sharp punch of the same diameter. Additionally, the actual extraction step is facilitated because the attachments of the surrounding tissue are more deeply broken than with a sharp punch, which operates more superficially. The disclosed system operates significantly faster than prior systems. Even if the actual cutting step may, in some cases, be slightly slower than with "sharp" punches, the shortening of the extraction step shortens the total extraction operating time. With prior systems, an experienced practitioner can extract up to 600 grafts per hour when the extraction step is separated from the cutting step (that is to say, the cutting step carried out with the punch comes to a stop during the extraction step with another tool or part of a tool). In contrast, the tool according to the disclosed technology can permit hourly follicular extraction rates of around 1000 grafts per hour.

The use of the disclosed hybrid trumpet punch can be particularly effective in cases that are generally difficult to treat. These include extraction of old grafts that are too voluminous, of hair grafts in African patients, and of beard grafts.

In the first case, the hair is often spaced further apart from each other than in a conventional situation. Furthermore, the internal micro-scars increase the strength of the attachment of the hair to the surrounding tissue. Among African patients, the hairs are highly curved in the shape of commas and their extraction is often extremely difficult, if not impossible, with the conventional technique of sharp punches. Finally, as to beard hairs, the hairs extracted almost never have lesions.

Those skilled in the art will recognize that the disclosed embodiments are illustrative and do not limit the scope of the disclosed technology. It is contemplated that various embodiments can be combined. The scope of the disclosed technology will be defined by the claims, which are appended hereto.

What is claimed is:

1. An apparatus for harvesting hair grafts from an epidermis, the apparatus comprising:
   a hollow tubular structure having a central axis; and
   an end structure attached to an end of the hollow tubular structure and terminating at a flat annular face that is substantially in a plane perpendicular to the central axis, wherein the face has a sharp outer edge and wherein an inner surface of the end structure inward from the flat annular face connects with an inner surface of the hollow tubular structure,
   wherein an outer diameter of the flat annular face is larger than an outer diameter of the hollow tubular structure, and
   wherein each portion of the flat annular face is at an angle relative to the central axis of 85° to 95°.

2. The apparatus according to claim 1, wherein the flat annular face is perpendicular to the central axis.

3. The apparatus according to claim 1, wherein the flat annular face has a thickness of at least 50 µm.

4. The apparatus according to claim 1, wherein the hollow tubular structure has the outer diameter between 0.7 mm and 1.4 mm and a wall thickness between 50 µm and 150 µm, and wherein the sharp outer edge of the flat annular face of the end structure has the outer diameter that is greater than the outer diameter of the hollow tubular structure by at most 200 µm.

5. The apparatus according to claim 1, wherein the end structure has a height of less than 1000 µm.

6. The apparatus according to claim 1, wherein the inner surface of the end structure inward from the flat annular face is substantially shaped as a half catenoid.

7. The apparatus according to claim 1, wherein the hollow tubular structure includes one or more windows.

8. The apparatus according to claim 1, wherein the sharp outer edge of the end structure has a toothed configuration having one or more teeth.

9. The apparatus according to claim 1, wherein the sharp outer edge of the end structure is substantially circular.

10. The apparatus according to claim 1, further comprising a motor coupled to the end structure that causes the end structure to rotate successively between clockwise and counterclockwise rotations.

11. The apparatus according to claim 10, wherein the motor is capable of being controlled to vary an amount of rotation of the end structure, wherein each clockwise or counterclockwise rotation is capable of rotating more than 30° but less than 360°.

12. The apparatus according to claim 10, further comprising a pedal coupled to the motor, the pedal controlling rotation of the end structure, wherein a depression of the pedal corresponds to a proportional change in a speed of the rotation of the end structure.

13. The apparatus according to claim 10, further comprising a pedal coupled to the motor, the pedal controlling rotation of the end structure, wherein a depression of the pedal corresponds to an exponential increase in a speed of the rotation of the end structure.

14. The apparatus according to claim 13, wherein the pedal is configurable to adjust the exponential correlation between the depression of the pedal and the increase in the speed of the rotation of the end structure, the pedal being configurable to select one of at least two exponential correlations.

15. The apparatus according to claim 13, wherein the speed of the rotation of the end structure is adjustable between 60 clockwise-counter-clockwise rotations per minute and 300 clockwise-counter-clockwise rotations per minute.

16. The apparatus according to claim 1, further comprising:
   a suction chamber attached to an end of the hollow tubular structure opposite the end structure; and
   a suction device coupled to the suction chamber.

17. The apparatus according to claim 1, further comprising a size indicator which indicates a size of the end structure.

18. The apparatus according to claim 1, further comprising a plurality of depth indicators on the hollow tubular structure which indicate depth at which the end structure has been inserted below an epidermis.

* * * * *